US00PP20977P2

(12) United States Plant Patent
Benardella

(10) Patent No.: US PP20,977 P2
(45) Date of Patent: May 4, 2010

(54) ROSE PLANT NAMED 'BENRYE'
(50) Latin Name: *Rosa hybrida*
Varietal Denomination: BENrye

(75) Inventor: Frank Benardella, Millstone Township, NJ (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 0 days.

(21) Appl. No.: 12/319,023

(22) Filed: Dec. 31, 2008

(51) Int. Cl.
*A01H 5/00* (2006.01)

(52) U.S. Cl. ..... Plt./137
(58) Field of Classification Search ..... Plt./137
See application file for complete search history.

*Primary Examiner*—Annette H Para

(57) ABSTRACT

This new rose plant is of an upright and spreading growing habit. It bears fragrant pink flowers with hybrid tea form, singly and in loose sprays. These flowers are slow to open and long lasting on the plant, making it an excellent decoration in the garden. They last very well as cut flowers, and lend their fragrant perfume to their surroundings.

1 Drawing Sheet

CROSS REFERENCE

The pollen parent of this new invention is a fragrant, orange-red, hybrid tea rose, 'Laguna' (code name 'KORmulen', not patented). A number of plants, related through 'Laguna', have been marketed from the same breeding program from which this new rose originated:

Those that are direct descendants of 'Laguana' as pollen parent are 'BENjen' (U.S. Plant Pat. No. 5,857, expired), a pink-blend, miniature rose; 'BENblack' (U.S. Plant Pat. No. 5,925, expired), a dark red miniature rose; 'BENalav' (U.S. Plant Pat. No. 6,517), a mauve miniature rose; and 'BENfig' (U.S. Plant Pat. No. 8,020), a miniature rose having white flowers edged with light pink.

A single rose plant from this same breeding program that is a direct descendant of 'Laguana' as seed parent is a red and white striped, hybrid tea rose named 'Tinseltown' (not registered nor patented).

All the above-mentioned roses have hybrid tea form. This new invention has superb hybrid tea form, but with flowers of a clear medium pink, quite different from the above listed roses. The flowers and foliage are similar in size to those of 'Tinseltown' but the plant habit of this new invention is more like that of a floribunda, whereas 'Tinseltown' is a hybrid tea. The other roses listed above as descendents of 'Laguna' are all miniature roses with much smaller flowers and foliage. The branching and flowering habit of 'BENjen' is similar to that of this new invention.

Genus and species: *Rosa hybrida.*

Varietal denomination: 'BENrye'.

BACKGROUND OF THE INVENTION

The present invention relates to a new and distinct variety of hardy, bush-type rose plant. This new variety is from a single seedling originated by Frank A. Benardella under controlled conditions in a greenhouse in Millstone Township (formerly Englishtown), N.J., by crossing the following two rose plants:

The seed parent of this new invention is a deep pink miniature rose, created in this breeding program in 1994, and registered as 'BENmgolf' (not patented). It is sold in New Zealand and South America under the trade name of Perfection.

The pollen parent of this new invention is a fragrant, orange-red, hybrid tea rose, registered as 'Laguna' (code name 'KORmulen', not patented).

The primary goal of this breeding program is to produce unique roses with award winning, hybrid tea form on plants having favorable attributes that will increase public appeal. To achieve this goal roses are selected for this hybridizing program primarily for their award winning, hybrid tea form. Pertaining to this particular cross, the pollen parent for this new invention, Laguna, was used because it has been noted to pass on the trait of hybrid tea flower form in a wide range of colors. As the trade name for the seed parent denotes, the flowers on Perfection are considered to be near perfect in form. It was also selected for its diminutive size, to give the potential to develop a wider assortment of classifications, including miniature or Mini-Flora roses. Both parent plants bear their flowers, primarily, one to a stem.

This new invention is well branched, in a manner similar to its seed parent. It has the thick, glossy foliage and upright growing habit, similar to its pollen parent. This resulting new cultivar has been named 'BENrye', with the trade name of Flawless.

SUMMARY OF THE INVENTION

This present invention relates to a new and distinct variety of a hardy, bush type, rose plant, which has several features that distinguish it from other presently available roses. The most significant distinction may be seen in its "flawless", hybrid tea-formed, medium-pink flowers. The manner in which these flowers unfurl sets them apart from most other flowers of this size and in this color class. Other characteristics that help distinguish it from all other varieties of which I am aware are:

Its moderately strong fragrance.

Its flowers of a medium pink with little fade.

An abundance of buds and blooms.

Flowers that open slowly and last quite a long time on the plant.

Flowers that last a week or more as cut flowers.

A rapid repeat bloom cycle.

Healthy, dark-green foliage.

A plant that grows and blooms very well, in both a greenhouse and outdoors, as a perennial garden decoration or in large containers.

BRIEF DESCRIPTION OF THE DRAWING

The accompanying illustration was taken in September, and is of a 3-year-old plant of this new invention, growing in the ground in Arroyo Grande, Calif. Flowers and foliage of this new invention are visible in various stages of development. Color is as nearly correct as it is possible to make in a color illustration of the character.

BOTANICAL DESCRIPTION OF THE PLANT

Unless otherwise noted, the following observations, measurements, values and comparisons are from a four-year-old plant of *Rosa hybrida,* 'BENrye', as grown outdoors in Ipswich, Mass. From April through July, 2008, the plant was grown in a 12-inch plastic nursery container in artificial soil mix, and then transplanted into the ground where observation was continued through November. Phenotypic expression may vary with environmental, cultural, and climatic conditions. Color references are made using The Royal Horticultural Society Colour Chart, except where common terms of color are used.

FLOWERS

BLOOMING HABIT is fast repeat to near continuous. In the summer, flowers are borne in clusters of two to four as well as singly. In the fall, flowers were born also in loose sprays of three to five with the central stem often terminating in a cluster of flowers and buds, usually of three, but rarely with more than a total of six buds and flowers within each spray.

BUDS are ovate, with an attenuate apex and are truncated at the base. Diameters have been measured 16/32 to 17/32 inch at their widest point while the plant was growing in the container, and about 19/32 inch after it was planted into the ground. Bud lengths were measured from 24/32 to 25/32 inch, throughout, when they were borne singly and only 18/32 inch long when borne in a cluster.

SEPALS: The flower has five sepals attached to the outer edge of the receptacle. They extend ¼ inch beyond the tip of the bud on the plant directly out of a California greenhouse, and only 11/32 inch beyond the tip of the bud while growing outside in the container, in Ipswich, Mass. They open ahead of the petals, reflex back to perpendicular with the receptacle, and flex back from that point with the petals. If a hip begins to form, the sepals will return to an upright position. Sepals are ovate-lanceolate with a truncated base. The three inner sepals have apiculate apices, narrowing quickly to a point. Their margins are ciliate with no foliar appendages. The two outer sepals have foliated margins and lanceolate apices; the apex of one of them may be longer than the entire sepal and usually has a serrated margin. The outside surface of the sepals is matte, with a coarse texture. The center of the sepals is a Scheele's Green near 144B; the area between this central area and the margins is darker with irregular and non-geometrical streaks that may be either near 146A and near 146B or near 144A and near 144B. The inside surface of the sepal is between 144A and 146B, muted by its fine pubescent covering. Sepals are permanently attached to the receptacle.

The RECEPTACLE is cone shaped. At its widest point, the diameter is 13/32 inch when borne singly and 11/32 to 12/32 inch when borne in clusters, both tapering to 7/32 to connect evenly to the peduncle. The height is usually about 15/32 inch. The color is near 144B and the surface is semi-glossy and glabrous. Unless a hip begins to form, receptacles will dry and remain attached to the peduncle.

PEDUNCLES are strong and straight or may be curved slightly sunward. The length of the peduncle is about 2 5/32 inches when borne singly and between 1 21/32 and 2 inches when borne in clusters. The diameter right below the receptacle is near 6/32 inch, tapering to 5/32 inch at connection to the stem when borne singly and tapering to 4/32 inch when borne in clusters. The color is a medium yellow-green. Interestingly, the color was found to be lightest on those borne singly, near 146D. In clusters, a color near 144A was observed on a peduncle exposed to the most sun and near 146C on a peduncle that was shaded from the sun by the plant itself. Cooler temperatures of fall found the sunward side lightly flushed with near 185A, Chrysanthemum Crimson. The surface of the peduncle is speckled with translucent, stipitate glands of varying lengths, being either near 184B or near 184C, with dark brown tips near 200A. There is an occasional hair. Peduncles usually dry and remain indefinitely attached to the plant.

BLOOM size varies from 3⅛ to 4¼ inches across, with a profile depth between 1 5/32 to 2 9/16 inches. The larger blooms are those borne singly or the central bloom of a spray or cluster. The flowers open slowly, sometimes taking 20 days to go from the time the sepals divide to half open, at exhibition stage. From that point, the flower lasts an additional 8 days or more before the petals begin to fade. Overall, a flower is often attractive on the plant for up to 30 days. The blooms start very high centered, open with a rounded upper profile and a flattened concave lower profile. Full open they have a flattened upper profile and a flattened-concave lower profile. Petal counts were noted to be 17 to 22 with 2 to 7 petaloids. Fragrance is moderate to strong and is raspberry and other fragrances.

PETALS are of a medium thickness and have excellent substance. Outer petals are broad fan shaped and inner petals are obovate. All petals have rounded, slightly scalloped margins. An acute apex is sometimes discernable. Outer margins recurve somewhat, decreasing toward the center of the flower, with margins of the inner petals remaining straight. Bases of the outer petals are rounded and become cordate on the inner petals. Both adaxial and abaxial surfaces are satiny and glabrous, with the abaxial surface being a bit rugose, and becoming leathery as it fades. Veins are slightly recessed on the adaxial surface. Veins on the abaxial surface protrude somewhat. During the first few days, the width of the outer petals varies between 1 13/32 and 1 18/32 inches but length is more uniformly between 1 12/32 and 1 13/32 inches. Petals are slow to detach form the receptacle.

COLOR changes from a rich Cardinal Red, near 53C, when the sepals first divide to a rich medium pink. During the first few days, after the sepals have separated but still before the petals have begun to unfurl, both surfaces are a rich rose pink. The adaxial surface is between 55A and 52B. The basal area and point of attachment are a yellow-green, near 154C, with veins in the basal area of a deep yellow-green, near 147A. The abaxial surface is Carmine, near 52B, with a basal area of near 154D. Veins on the abaxial surface are near 62D. The point of attachment is a near 147A. Inner petals have the same coloring but with a slightly larger basal area.

When half blown the color of the adaxial surface lightens somewhat to near 55C, a Neyron Rose, with a light Chartreuse-Yellow basal area near 2D and a darker point of attachment near 2B. The reverse is near 62A, Rhodamine Pink, with a basal area of near 2D. Veins become noticeable, starting as white, near 155D, at the base and becoming a very light pink, near 65D, toward the margins; primary veins radiate from a single main vein that originates at the point of attachment. The point of attachment is near 142B, an Agathia Green. The adaxial surface of the inner petals is a bit darker, near 55B. Their reverse is near 62C along the margins and becoming lighter toward the base, where it blends with the near 2D of the basal area. Veins are a Primrose Yellow, near 4D, at the base and become near 155D toward the margins. The point of attachment is near 2A.

When full blown, the adaxial surface of the outer petals remains near 55C. The basal area and point of attachment are near 4D. Veins in the basal area are near 144B. The reverse is near 63D, a Spiraea Red, becoming near 63B along the margins. The basal area and point of attachment is near 2D. Veins are near 2D beginning in the basal area and become near 158D as they proceed through the petal. The abaxial surface of the inner petals of the full-blown bloom is near 63D with a suffusion near 62A along the margins. The basal area is near 4D. The point of attachment is near 4B, which continues along the main vein through the basal area, before it begins to lighten to near 155D. The reverse of the inner petals is near 62A, with a basal area of Mimosa Yellow, near 8D, and point of attachment near 8B; veins appear near 155D.

When grown outdoors in full sun, the outer petals, in particular, become a bit rugose and show some "weathered" characteristics. Colors are also a bit different. The adaxial surface may be between 55B and 61D, and a bit darker along the margin, beginning near 58B along the outer margin and lightening to near 58C toward the base. The basal area and point of attachment are a green-yellow, near 1A, with veins in the basal area of a bright green, near 143A. The abaxial surface is a Neyron Rose, between 58C and 55B, and lightens as it progresses down the petal, becoming between 58D and 55B in the basal area. Veins on the abaxial surface are also near 55D. The point of attachment is a light yellow green, near 154B, and extends up into the basal area. There are occasionally random streaks of a Tyrian Purple, near 61C, on either surface of the outer petals. Occasionally a wide streak of a greenish-white is found going from the basal area to the outer margin, but not always to the apex. This streak may be near 155C or near 157D, and occasionally is light green, near 194C, starting down from the outer margin.

Petals at the center of these flowers are near 54C, Spinel Red, on the adaxial surface, with a basal area of near 1C and point of attachment of near 2A. Occasional streaks of near 2D may be found on some petals, often widening as they go up the petal. The reverse of the inner petals is darker, near 48C, Empire Rose, with a darker color, between 54B and 58B, along the margins, and veins near 58C. The basal area is near 154C, which blends up into the petal. The point of attachment is near 154B, a Chartreuse Green.

PETALOIDS are the same color and texture as the inner petals but may have random streaking, similar to that seen on the outer petals. Size and shapes are quite variable. They may be as only half of a petal with one edge being along the main vein. They may be as an inner petal except with part of or one-half of the outer margin being very ruffled. They may be just generally small, deformed, and attached by a filament, having one side a sterile anther or part thereof and the other side as a small piece or large part of a petal. They may be attached with a filament and have a sterile anther at the apex.

REPRODUCTIVE ORGANS

ANDROECIUM: STAMENS are arranged around the outer edge of the receptacle. Quantities were noted to vary between 164 and 195. The color of the ANTHERS is near 163A, a dull color from the Greyed-Orange group. POLLEN SACS are an Indian Yellow, near 17C. FILAMENTS are lighter than the anthers, between 163B and 162A, with a length of about 5/32 inch within a few days of the sepals rolling back, and become near 10/32 inch long in the full open bloom.

GYNOECIUM: PISTILS originate from within the center of the top of the receptacle. Their quantity ranges from ½ to ⅓ the number of stamens. STYLES are thin and straight. Their length ranges from 3/32 inch on the newly opened flower to 6/32 inch on the full open bloom. Their color is Currant Red, near 47A, right below the stigma, and becomes a very light yellow-green towards the base. STIGMAS are a grayed green-yellow, near 160C.

HIPS were not observed.

PLANT

The plant of this new rose is vigorous with an upright and spreading growing habit as it becomes very well branched. The mature plant can be 22 to 40 inches tall, depending on growing conditions. The diameter of the base of main canes is 22/32 to 25/32 inch, of primary lateral canes is 15/32 to 16/32 inch, and of flowering stems is 3/16 inch. The length of the flowering stems varies from nearly 12 inches to 13½ inches when borne singly and near 11 inches when in a spray of three. There are six or seven nodes on each flowering stem, regardless of the length. The surface of new wood is glossy and smooth, and of a yellow-green color between 146A and 146B. Old wood is coarse and a bit darker, near 146A. Lenticels develop in vertical, near parallel stripes during the second year of growth and usually completely cover the canes by the end of the third year. The color of the lenticels is a green-gray, near 197A. This new cultivar was tested hardy to zone 5.

FOLIAGE is pinnately compound, usually with five or seven leaflets, and occasionally with only three leaflets. Mature leaves were measured from 5¾ inches to 7¼ inches long, regardless of whether there were seven or five leaflets. Leaflets are ovate. The base of the leaflets immediately below the terminal leaflet is usually obtuse. Serration is mostly simple, with a gland on the tip of each serrate. The length of mature terminal leaflets was measured from 2 13/16 to 3⅝ inches, relative to the length of the entire leaf. Widths of those terminal leaflets varied from 1½ to 2 3/16 inches, not relative to their lengths. The upper adaxial surfaces are semi-glossy and abaxial surfaces are matte. The color of the adaxial surface of young leaflets is a medium green, between 144A and 137A, with no anthocyanin coloration. The abaxial surface is a more yellow-green, near 147B and is lightly flushed with a deep orange-brown, near 176B. Adaxial surfaces of older foliage become darker green, between 147A and 137A, and at maturity are near 137A. The abaxial surfaces become somewhat lighter, first between 147B and 138A and flushed lightly with a brownish-red, near 178A, and veins flushed even lighter, near 174A. At maturity the entire abaxial surface lightens to between 147C and 138C with no flushing.

PETIOLES are between 1½ and 2 3/16 inches long, usually in direct proportion to the length of the leaf. The girth varies from 6/64 to 7/64 inch, relative to the length of the petiole. On seven-leaflet leaves, aciculiform foliar appendages were observed attached to the petiole between the stipules and the point of attachment of the basal leaflets. The length of the RACHIS varies from 1 1/16 to 1 17/32 inch on the five-leaflet leaves and from 1 9/16 to 2 7/32 inch on the seven-leaflet leaves.

Girth of all rachises varied between 5/64 and 7/64 inch. PETIOLULES to the terminal leaflets were longer on the five-leaflet leaves, varying from 1 1/16 to 1 3/16 inches; on the seven-leaflet leaves they varied from 21/32 to 30/32 inch long. Girth of the petiolules generally was 1/64 inch less than the girth of the corresponding rachis. The color of all ridges and grooves on the adaxial surfaces of the leaves is near the same. On new growth they are flushed a purple-red, near 184A, with the deepest flushing on the petiolules and least flushing on the petioles. The under surface is flushed a brown-red, near 176B. On mature leaves, the anthocyanin coloration is gone, the adaxial surfaces are near 139A, and the abaxial surfaces are between 138B and 147B.

STIPULES are paired at the base of the petioles, usually with about 25/32 to 26/32 inch attached and an additional 6/32 to 7/32 angled outward at thirty to thirty-five degrees. The part angled outward varied about 1/32 inch within each pair. The adaxial surface is between 144A and 144B and the abaxial surface is between 147C and 144C. Margins are entire and lined with near evenly spaced stipitate glands.

PRICKLES are deltoidal with an acute point, are often angled slightly downward, and usually have slightly concave upper and lower profiles. On main canes and primary laterals, there are anywhere from eight to eighteen in two inches of stem; their length was 10/32 to 11/32 inches, on a narrow-obovate base that is 1/32 inch shorter than the length of that prickle. On flowering stems there may be two to eleven in two inches of stem, with lengths varying from 1/32 to 5/16 inch. When young, the prickles are a brownish-red, near 178A. When mature, they become a dark brown, near 200C, and when old they become a green-gray, near 197A, the same color as the lenticels.

In Ipswich, Mass., the plant was noted to have above average resistance to blackspot and powdery and downy mildews. In California, resistance was average to blackspot and powdery and downy mildews but well above average to rust. Rust was not observed in Massachusetts.

The invention claimed is:

1. A new and distinct variety of rose plant is claimed, substantially as described and illustrated herein.

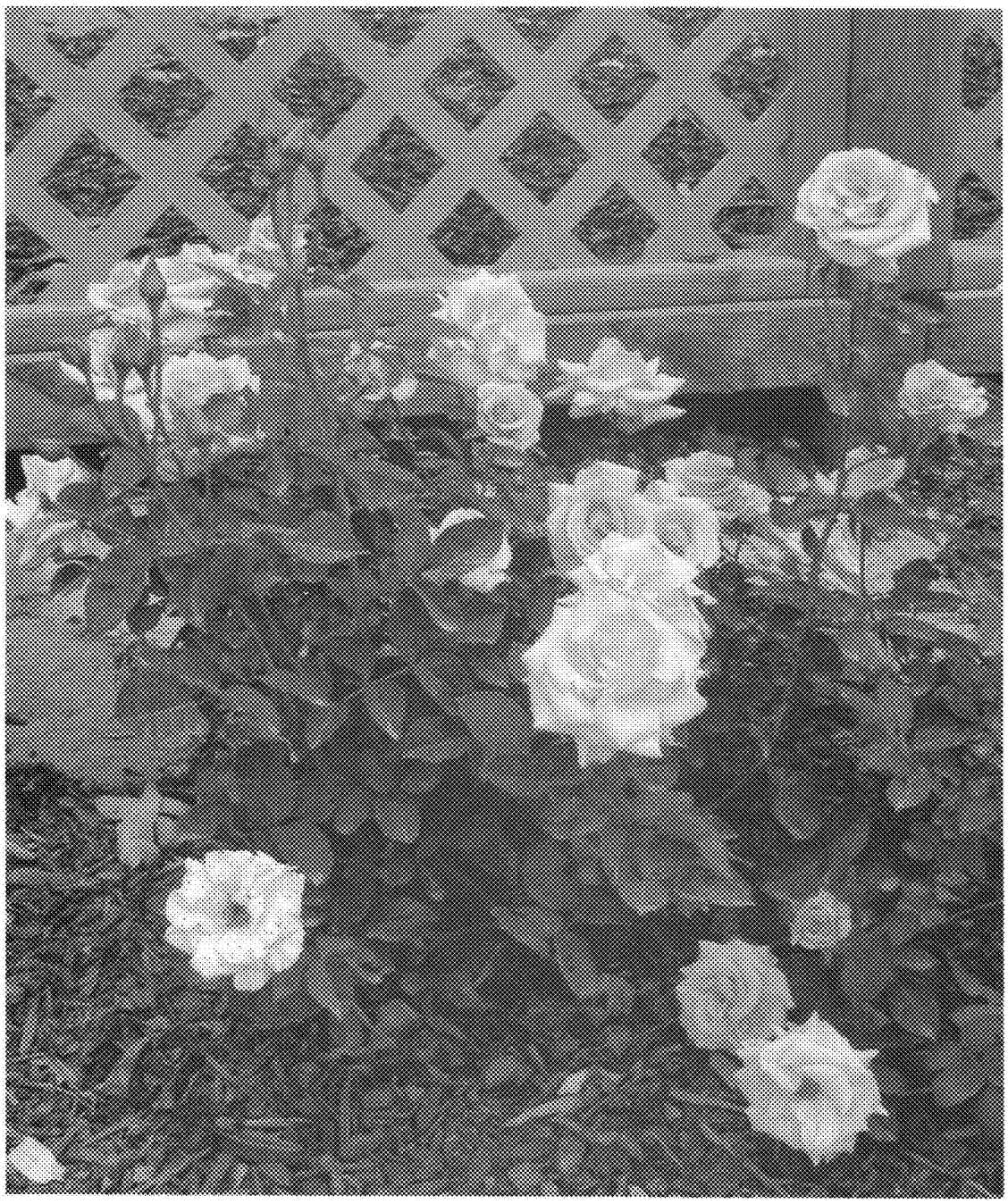

* * * * *